United States Patent [19]

Siesler et al.

[11] Patent Number: 5,739,537
[45] Date of Patent: Apr. 14, 1998

[54] NIR ABSORBANCE MEASURING INSTRUMENT WITH ATR PROBE

[75] Inventors: Heinz W. Siesler, Essen, Germany; Ursula Eschenauer, Baltimore, Md.

[73] Assignee: Perstorp Analytical, Inc., Silver Spring, Md.

[21] Appl. No.: 576,489

[22] Filed: Dec. 21, 1995

[51] Int. Cl.⁶ .................................................. G01N 21/17
[52] U.S. Cl. ........................... 250/341.8; 250/339.11
[58] Field of Search ........................... 250/341.2, 341.8, 250/339.11, 339.12

[56] References Cited

U.S. PATENT DOCUMENTS

| | | | |
|---|---|---|---|
| 3,460,893 | 8/1969 | Wilkes, Jr. | 250/338.1 |
| 4,844,869 | 7/1989 | Glass . | |
| 5,051,551 | 9/1991 | Doyle | 250/341.2 |
| 5,097,129 | 3/1992 | De Vries et al. | 250/341.8 X |
| 5,416,579 | 5/1995 | Barshad et al. | 356/300 |
| 5,436,454 | 7/1995 | Bornstein et al. | 250/339.12 |
| 5,585,634 | 12/1996 | Stevenson et al. | 250/341.8 X |

FOREIGN PATENT DOCUMENTS

| | | | |
|---|---|---|---|
| 4038354 | 6/1992 | Germany . | |
| 63-274840 | 11/1988 | Japan . | |
| 257947 | 2/1990 | Japan | 356/246 |
| 4-186140 | 7/1992 | Japan . | |
| 5-142142 | 6/1993 | Japan . | |

*Primary Examiner*—Edward J. Glick
*Attorney, Agent, or Firm*—Lane, Aitken & McCann

[57] ABSTRACT

In a near infrared absorbance measurement instrument, an attenuated internal reflectance probe comprises a quartz rod having an inexpensive low purity central core surrounded by two high purity quartz layers. Narrow band infrared light is transmitted axially through the outer layer to cause the light to undergo total internal reflection from the inner and outer surfaces of the outer layer. A near infrared light detector measures the light transmitted through the outer layer to obtain a measurement of the absorbance of the fluid in contact with the outer surface of the outer layer without any interference from suspended particles or bubbles in the fluid being measured.

12 Claims, 5 Drawing Sheets

NIR ABSORBANCE MEASURING INSTRUMENT WITH ATR PROBE

BACKGROUND OF THE INVENTION

This invention relates to a sensor for making near infrared absorbance measurements on fluids by means of a probe designed to eliminate interference occasioned by solid particles and gaseous particles, otherwise known as bubbles.

In accordance with the invention, the interference from particles is eliminated by making the measurements by attenuated total reflection (ATR). The probe of the invention comprises a cylinder made of a high purity near infrared light transmitting material, such as high purity quartz or silica. Near infrared light of a narrow band wave length from a spectrometer is transmitted axially into the cylinder by fiber optics causing the near infrared light to undergo multiple, total internal reflections at the inner and outer walls of the cylinder. Light transmitted through the cylinder will be attenuated each time it undergoes total internal reflection at the outer surface of the cylinder by an amount depending upon the absorbance of the fluid in contact with the outer wall of the cylinder. Accordingly, the near infrared light transmitted through the cylinder will be attenuated to a degree depending upon the absorbance of the fluid.

In accordance with the preferred embodiment of the invention, the cylinder is supported by an inexpensive quartz core which is covered by first and second thin layers of high purity quartz. The first layer, which has a thickness of about 20 microns, is selected to have a refractive index smaller than the second outer high purity quartz layer, which has a thickness of about 100 microns. The near infrared light from the spectrometer is transmitted through the outer quartz layer. Because of the presence of the inner quartz layer separating the outer quartz layer from the quartz core, impurities in the core have no effect on the total internal reflections occurring at the interface between the inner cylindrical layer and the outer cylindrical layer. This construction enables the cylinder through which the near infrared light is transmitted to be made thin and, thus, a large number of total internal reflections at the outer surface are achieved over a relatively short length for the quartz layer. The length of the cylinder can be made only 20 centimeters long and obtain measurements extending over the near infrared wavelength range.

DESCRIPTION OF THE PREFERRED EMBODIMENTS

Figure 1:
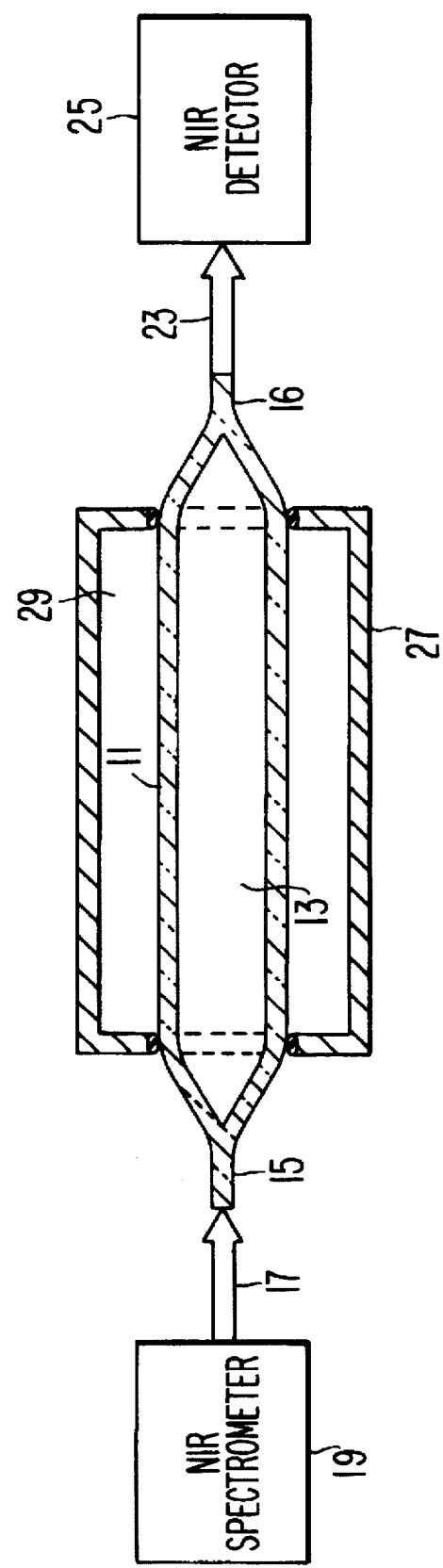
FIG. 1 is an axial section schematically illustrating an early embodiment of the probe of the present invention.

In the embodiment of the invention shown in FIG. 1, a quartz tube 11 defines an evacuated chamber 13 which is surrounded by the walls of the tube. The ends of the tube 11 neck down into coaxial solid quartz rod-shaped ends 15 and 16. One end 15 is coupled by means of a fiber optic cable 17 to a spectrometer 19 and the other end 21 is coupled by means of fiber optic cable 23 to a detector 25. The NIR spectrometer 19 transmits a narrow wavelength band of near infrared light through the fiber optic cable 17 into the quartz rod-shaped end 15 from which the light is transmitted through the cylindrical walls of the tube 11 to the rod-shaped end 16. The spectrometer 19 may be of the rotating grating type and varies the center wavelength of narrow band NIR light throughout the NIR spectrum. The amplitude of the transmitted light is detected by the detector at different incrementally spaced wavelengths distributed throughout the near infrared spectrum. While being transmitted through the cylindrical wall of the tube 11, the near infrared light experiences multiple total internal reflection from the outer and inner surfaces of the cylindrical surface. The outer cylindrical walls of the tube 11 is surrounded by an enclosure 27 defining a chamber 29 interfacing with the outer surface of the tube 11. Fluid to be measured is provided in the chamber 29 and the narrow band near infrared light being transmitted through the tube 11 will be partially absorbed each time it undergoes total internal reflection from the outer surface of the cylindrical wall. The amount of absorption will depend upon the absorbance of the fluid at the wavelength being transmitted through the walls of the tube 11. The light, after experiencing this absorption, will be transmitted from the rod shaped end 16 through the fiber optics 23 to the NIR detector 25, which detects the amplitude of the received NIR light. Measurements are preferably made at wavelength increments distributed throughout the NIR spectrum. Because the absorbance is measured by total internal reflection, the absorbance is measured with very little penetration of the light waves into the fluid within the chamber 29 and, as a result, bubbles or particles suspended in the fluid within the chamber 29 have no effect on the absorbance measurement.

Figure 2:
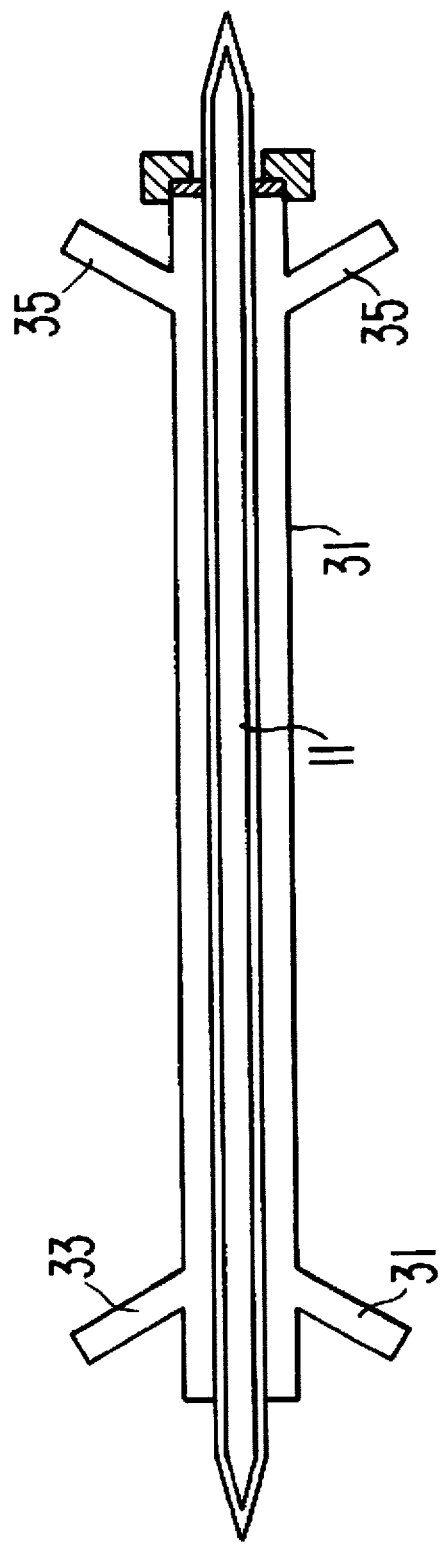
FIG. 2 also illustrates an early embodiment of the invention designed for measuring flowing fluids.

The embodiment illustrated in FIG. 2 is similar to that in FIG. 1 except that the system of FIG. 2 has been adapted specifically for measuring flowing fluids. As shown in FIG. 2, the evacuated quartz tube 11 is surrounded by a jacket 31 which is provided with fluid inlets 33 and fluid outlets 35. Thus, fluid can be caused to flow in the chamber between the jacket 31 and the tube 11 to permit absorption measurements to be made on the flowing fluid by the ATR effect.

In the embodiments of FIGS. 1 and 2, the wall thickness of the quartz tube has to be thick enough to support the stress applied to the tube by the evacuated internal chamber. The thicker the wall of the tube, the fewer total internal reflections that will occur as the light travels through the cylindrical tube walls. In order to achieve sufficient amount of total internal reflection at the longer near infrared wavelengths, the tube has to be made very long, for example, up to 200 centimeters. In addition, the drawing out of the tube to form the rod shaped ends is a difficult manufacturing process.

Figure 3:
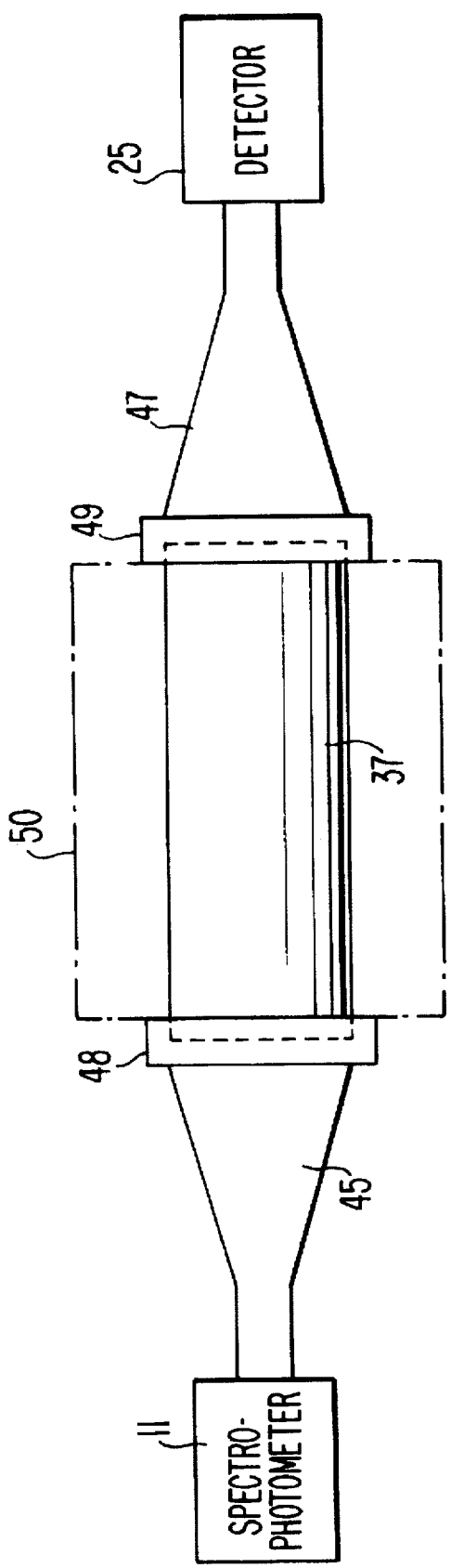
FIG. 3 schematically illustrates the preferred embodiment of the present invention.
Figure 4:
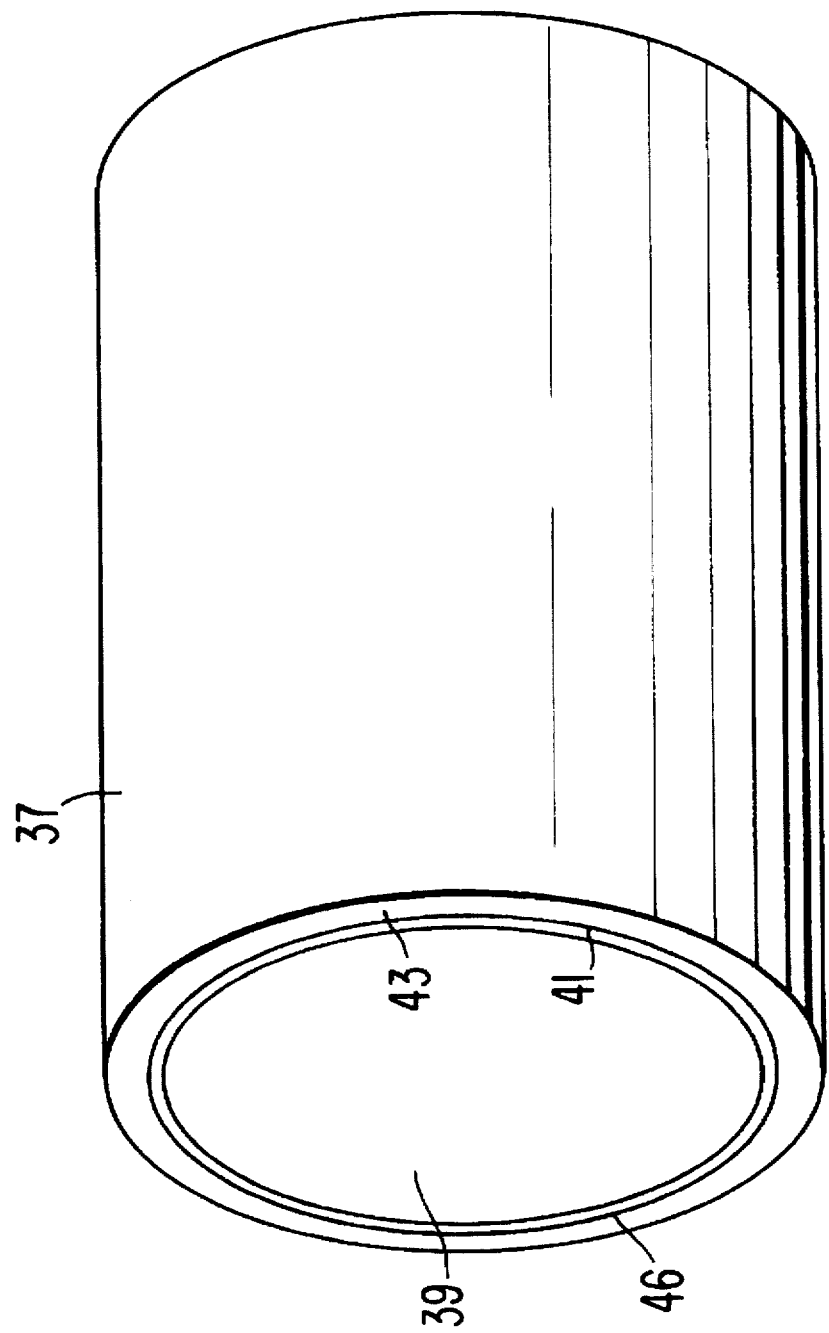
FIG. 4 is an isometric view in elevation of the sensor portion of the probe of the preferred embodiment.
Figure 5:
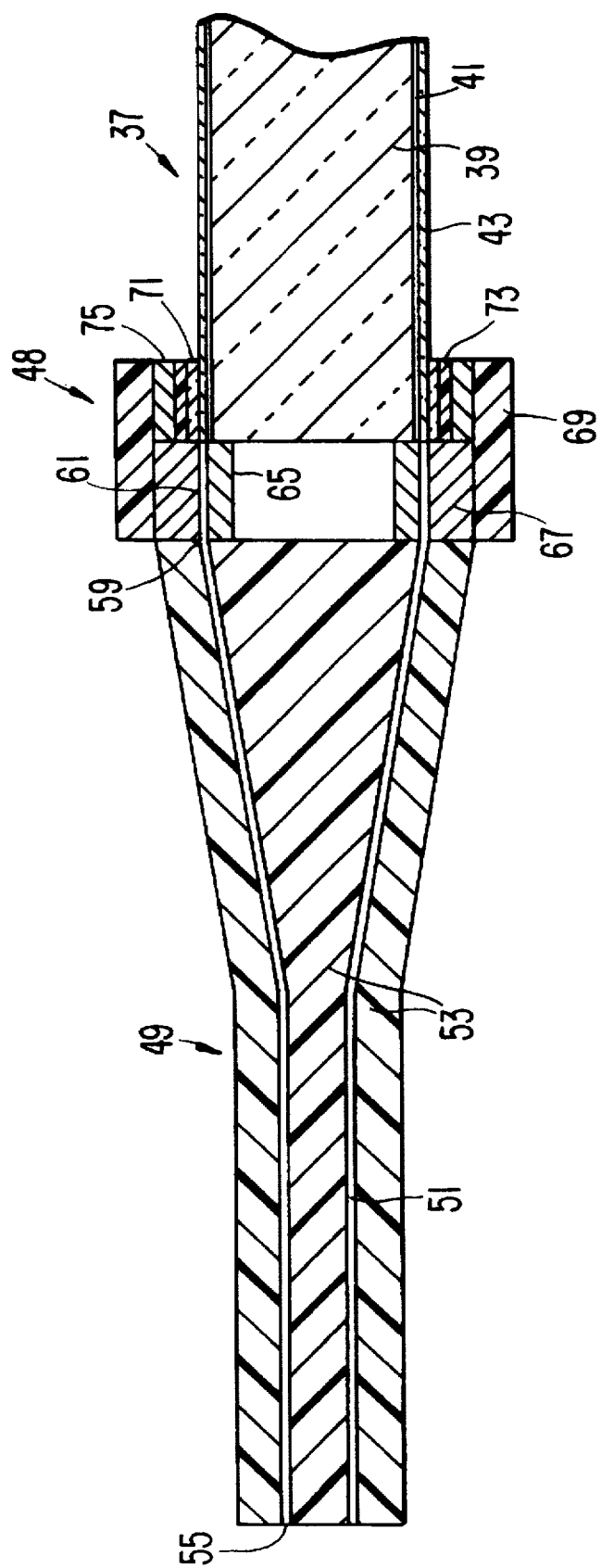
FIG. 5 is an axial sectional view showing the details of the coupling of the fiber optics to the cylindrical sensing portion of the probe of the invention.

In the preferred embodiment of the invention, as illustrated in FIGS. 3–5, the ATR probe comprises a solid quartz rod 37 comprising an inner solid cylinder 39 coated with two outer layers 41 and 43. The inner rod 39 is made of inexpensive quartz material of relatively low purity and is covered with a thin layer 41, approximately 20 microns thick, of high purity quartz and a second thicker outer layer 43 of high purity quartz having a thickness of about 100 microns. The refractive index of the inner layer 41 is selected to be smaller than that of the outer layer 43 so that light transmitted through the outer layer 43 will be totally internally reflected at the interface 46 between the inner layer 41 and the outer layer 43. Narrow wave band near infrared light from the spectrometer 11 is transmitted through a fiber optic connector 45 into the outer layer 43 and is transmitted axially through the outer layer 43 to a fiber optic connector 47 which transmits the narrow band light to a near infrared light detector 25. The fiber optic connectors 45 and 47 are optically coupled to the outer layer 43 through adapters 48 and 49. The narrow band near infrared light undergoes multiple total internal reflection between the outer surface of the layer 43 and the interface 46 between the outer layer 43 and the inner layer 41. The transmitted light is not affected by the impurities in the core 39 because the core 39 is isolated from the total internal reflections occurring at the interface 46 by the high purity layer 41. The light transmitted through the outer layer 43 will be attenuated by the absorbance of the fluid contained in enclosure 50 in contact with the outer surface of the outer layer 43 and thus the degree of attenuation detected by the detector will be a measurement of the absorbance of the fluid.

As shown in FIG. 5, the fiber optic connector 45 comprises a sheath of optic fibers 51 enclosed in a plastic cladding 53. The optic fibers receive light from the spectrometer at a receiving end 55 and spread to a transmitting end 59 where they are optically doupled to a cylindrical ring of optical fibers 61 in a coupling adapter 48. In the adapter 63, the cylindrical ring of fibers 61 is sandwiched between an inner metal ring 65 and an outer metal ring 67 and the transmitting ends of the optic fibers 61 abut against the axial end of the outer cylindrical quartz layer 43. The adapter 48 has an outer cylindrical case 69 and may be any suitable material, such as plastic or metal. The casing 69 overlaps the end of the quartz rod 37 and sandwiched between the casing 69 and the outer cylindrical surface of the outer layer 43 of the quartz rod 37 are an inner quartz layer 71 of high purity covered by a plastic coating 73 and separated from the casing 69 by a metal ring 75. The quartz layer 71 has an isolating function preventing the total internal reflections which occur at the outer surface of the outer layer 43 within the overlap of the adapter 48 from being affected by the adapter.

The fiber optic coupler 47 and the fiber optic adapter 49 between the quartz rod 37 and the detector 25 are identical to the coupler 45 and the adapter 48, respectively.

Because the absorbance measurements are made by total internal reflection at the outer surface of the quartz rod 37, the absorbance of fluids in engagement with the rod 37 can be readily measured without interference from solid or gaseous particles.

Because the outer layer 43 can be made relatively thin, e.g., about 100 microns, the light being transmitted through the outer layer 43 will experience a relatively large number of total internal reflections from the outer surface upon traveling through a relatively short axial length and, as a result, the axial length of the sensitive part of the probe may be made relatively short, for example, only 10 to 20 centimeters, and still be effective in measuring the absorbance over the near infrared range.

As described above, the ATR probes of the invention are effective in measuring absorbance of fluids without interference from solid particles or bubbles suspended in the fluid. The probes also can be used with advantage to measure absorbance of fluids which do not contain particles or bubbles or are otherwise not subject to the problem of interference from particles or bubbles.

In the instruments described above, the NIR light is dispersed into narrow bandwidth increments before it is transmitted through the quartz cylinder. Alternatively, broad band NIR light can be transmitted through the quartz cylinder and the light disbursed by a spectrometer after passing the cylinder and then detected by a detector or detectors. These and other modifications may be made to the above described specific embodiment of the invention without departing from the spirit and scope of the invention as defined in the appended claims.

We claim:

1. An attenuated total internal reflectance measuring instrument comprising a light transmitting rod having a solid core portion and an adjacent high purity outer layer having an inner surface in engagement with said core portion and an outer surface, means to transmit near infrared light axially through said outer layer to cause said near infrared light to undergo total internal reflection at said inner surface and said outer surface, and means to detect the near infrared light transmitted through the outer layer.

2. An instrument as recited in claim 1, wherein said core portion comprises a core and an intermediate high purity layer separating said outer layer from said core.

3. An attenuated total reflectance instrument as recited in claim 2, wherein said core, said intermediate layer and said outer layer consist essentially of quartz.

4. An instrument as recited in claim 2, wherein said intermediate layer is thinner than said outer layer and has a lower index of refraction than said outer layer.

5. An instrument as recited in claim 4, wherein said core has lower purity than said intermediate layer and said outer layer.

6. An instrument as recited in claim 4, wherein said outer layer has a thickness of about 100 microns and said intermediate layer has a thickness of about 20 microns.

7. An instrument as recited in claim 1, further comprising fiber optics for transmitting near infrared light from a spectrometer to said outer layer and from said outer layer to said means to detect near infrared light.

8. A method of measuring absorbance of a fluid in the near infrared region containing gaseous or solid particles without interference from said particles comprising passing near infrared light axially through an elongated near infrared light transmitting element, said element comprising a rod having a solid core portion and an adjacent high purity outer layer in engagement with said core portion, said near infrared light being transmitted axially through said outer layer by being totally internally reflected from a wall of said outer layer, contacting said wall of said outer layer with said fluid while said fluid contains said particles whereby said near infrared light transmitted through said element is attenuated by the absorbance of said fluid, and detecting the amplitude of said near infrared light transmitted through said element.

9. A method as recited in claim 8, wherein said particles are gaseous particles.

10. A method as recited in claim 8, wherein said particles are solid particles.

11. A method as recited in claim 8, wherein said near infrared light is narrow band infrared light and is transmitted through said elongated element at different wavelengths to measure the absorbance of said fluid at different wavelengths.

12. An attenuated total internal reflection measuring instrument comprising a cylindrical light transmitting element having an inner cylindrical wall and an outer cylindrical wall and means to transmit near infrared light axially through said cylindrical element to cause near infrared light to undergo total internal reflection at said inner cylindrical wall and said outer cylindrical wall and means to detect near infrared light transmitted through said cylindrical element, and wherein said cylindrical element comprises an evacuated tube.

* * * * *